United States Patent [19]
Wolters et al.

[11] Patent Number: 6,130,350
[45] Date of Patent: Oct. 10, 2000

[54] PROCESS FOR PRODUCING 2-FLUORINE-1-CYCLOPROPANE CARBOXYLIC ACID DERIVATIVES BY REDUCTIVE DEHALOGENATION

[75] Inventors: Erich Wolters; Norbert Lui, both of Köln; Nikolaus Müller, Monheim, all of Germany

[73] Assignee: Bayer Aktiengesellschaft, Leverkusen, Germany

[21] Appl. No.: 09/180,810

[22] PCT Filed: Apr. 30, 1997

[86] PCT No.: PCT/EP97/02210

§ 371 Date: Nov. 16, 1998

§ 102(e) Date: Nov. 16, 1998

[87] PCT Pub. No.: WO97/44309

PCT Pub. Date: Nov. 27, 1997

[30] Foreign Application Priority Data

May 23, 1996 [DE] Germany ............... 196 20 798

[51] Int. Cl.$^7$ .................................................. C07C 69/74
[52] U.S. Cl. ............................................. 560/124; 562/506
[58] Field of Search ............................. 560/124; 562/506

[56] References Cited

U.S. PATENT DOCUMENTS

| | | | |
|---|---|---|---|
| 3,320,121 | 5/1967 | Douros | 562/506 |
| 3,567,740 | 3/1971 | Matsui et al. | 560/124 |
| 5,081,283 | 1/1992 | Gassen et al. | 560/124 |
| 5,159,111 | 10/1992 | Gassen et al. | 562/867 |
| 5,770,767 | 6/1998 | Itaya et al. | 562/506 |
| 5,780,669 | 7/1998 | Akiba et al. | 560/124 |

FOREIGN PATENT DOCUMENTS 712831  8/1993  European Pat. Off. .

OTHER PUBLICATIONS

Antimicrobial Agents & Chemotherapy, Dec. 1993, 37 (12), 2747–2753.
Antimicrobial Agents & Chemotherapy, Mar. 1994, 38 (3), 611–615.
J. Med. Chem. 37 (Sep. 20, 1994, pp. 3344–3352.
J. Am Chem. Soc. 89, Oct.–Dec., 1994, vol. p. 5719.
Tetrahedron Lett. (month unavailable) 2967, p. 1123.
J. Org. Chem. 35, No. 1, Jan. 1970, p. 33.
Synthesis, Oct. 1970, p. 499.
Chem. Ber. (month available) 1971, p. 1921.
Journal of Florine Chem. 49, Mar. 1990, p. 127.
Bulletin of the chemical Society of Japan, vol. 45, (1972) month unavailable, page 1926.

*Primary Examiner*—Gary Geist
*Assistant Examiner*—Taylor V Oh
*Attorney, Agent, or Firm*—Joseph C. Gil; Diderico van Eyl

[57] ABSTRACT

Cyclopropanecarboxylic acid derivatives are prepared by reacting halogenocyclopropanecarboxylic acid derivatives with metals in the presence of bases and with or without addition of hydrogen in an advantageous manner if the base is added during the reaction. By means of the process according to the invention, good yields and selectivities and a high proportion of cis isomers in the reaction product may be achieved.

7 Claims, No Drawings

PROCESS FOR PRODUCING 2-FLUORINE-1-CYCLOPROPANE CARBOXYLIC ACID DERIVATIVES BY REDUCTIVE DEHALOGENATION

FIELD OF THE INVENTION

The present invention relates to an improved process for preparing 2-fluoro-1-cyclopropanecarboxylic acid derivatives by reacting 2-halogeno-2-fluoro-1-cyclopropanecarboxylic acid derivatives with addition of a metal and a base.

BACKGROUND OF THE INVENTION

2-Fluoro-1-cyclopropanecarboxylic acid derivatives are intermediates for preparing pharmaceutical active compounds, in particular antiinfectives from the group consisting of the quinolones (see, eg., Antimicrobial Agents and Chemotherapy 37 (12), 2747 to 2753 (1993) and 38 (3), 611 to 615 (1994) and J. Med. Chem. 37 (20), 3344 to 3352 (1994)).

The reductive replacement of halogen in geminal halogeno-fluorocyclopropane derivatives by hydrogen has already been described in the literature.

One reaction is the method using tri-n-butyl-tin hydride (eg. J. Am. Chem. Soc. 89. 5719 (1967), Tetrahedron Lett. 1967, 1123, J. Org. Chem. 35, 33 (1970) and Synthesis 1970, 499). The use of tri-n-butyl-tin hydride is scarcely expedient, economically and ecologically, owing to its toxicity, its poor accessibility, which gives rise to high costs, and the large amount required.

Another method is the reaction using sodium in liquid ammonia (see, eg., Chem. Ber. 104, 1921 (1971)). This process also has the disadvantage that it is highly complex in the case of an industrial procedure.

In a further process, the dehalogenation is carried out using other metals, preferably Raney nickel, in the presence of hydrogen and a base (see, eg., J. Fluorine Chem. 49, 127 (1990) and WO 95/04712). Bull. Chem. Soc. Jap. 45, 1926 (1972) describes that, in the hydrogenolytic dehalogenation of 7-chloro-7-fluorobicyclo[4.1.0]heptane with Raney nickel, the desired product, 7-fluorobicyclo[4.1.0]heptane, was only obtained using 1,2-diaminoethane as base, and no reaction took place using other bases.

This process has the disadvantage that the selectivity is low. The selectivity can be increased if low temperature (eg. room temperature) is employed. However, this leads to incomplete conversion and to reaction times of 50 hours and more. Even when a large excess of Raney nickel and base are used, the conversion rate can only be increased slightly and the reaction time can only be shortened slightly. Thus, in the last-cited literature reference, when 852 mol % of Raney nickel and 6000% of 1,2-diaminoethane (each based on the starting material) are used, a conversion rate of only 58% is achieved in 24 hours at 18 to 22° C. According to WO 95/04712 also, large excesses of Raney nickel and 1,2-diaminoethane are used, more precisely 466 to 3785 mol % of Raney nickel and 300 to 1000 mol % of 1,2-diaminoethane.

However, it is essential that the highest possible conversion rate is achieved, since it is not possible to separate the desired products, in particular the cis isomers, from the starting materials by distillation with reasonable expenditure.

Although the reaction proceeds considerably faster if the reaction temperature is elevated, in which case the required amounts of Raney nickel and 1,2-diaminoethane can also be reduced, at the same time the selectivity greatly decreases. Thus, at 80° C., a yield of only 10% of theory is achieved (see J. Fluorine Chem. 49, 127 (1990)).

There is therefore still the requirement for a process which gives the desired product in good yields and selectivities in a short reaction time and with small amounts of metals and bases used.

SUMMARY OF THE INVENTION

A process has now been found for preparing cyclopropanecarboxylic acid derivatives of the formula

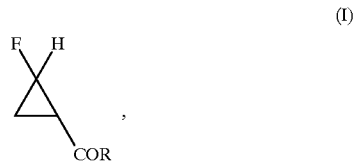

in which
R represents $OR^1$ or $NR^2R^3$, where $R^1$, $R^2$ and $R^3$ independently of one another each represent a linear or branched $C_1$–$C_4$-alkyl radical,
by reacting halogencyclopropanecarboxylic acid derivatives of the formula

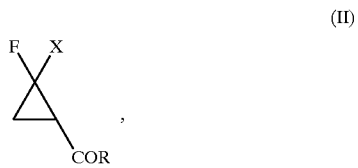

in which
R has the meaning specified under formula (I) and
X represents chlorine, bromine or iodine with addition of a metal and a base, which comprises adding the base during the reaction and working in a protic solvent.

Higher temperatures, ie. shorter reaction times, and decreased usage of metals and bases can then be employed, and, despite this, the products of the formula (I) can be obtained in good selectivities and yields.

DETAILED DESCRIPTION OF THE INVENTION $C_1$–$C_4$-Alkyl radicals mean, in particular, methyl, ethyl, propyl, isopropyl, butyl, isobutyl, s-butyl and t-butyl, preferably methyl and ethyl, very particularly preferably ethyl.

In the formula (I), X preferably represents chlorine and bromine, particularly preferably chlorine.

The metal to be used according to the invention can be, for example, one or more metals of the 2nd and/or 8th subgroup of the Periodic Table of the Elements, for instance zinc, iron, cobalt and/or nickel. The metals may if appropriate be applied to a support or can be present in a particularly active form, eg. in Raney form. Preferably, cobalt and/or nickel is/are used, particularly preferably nickel, and very particularly preferably Raney nickel.

Suitable bases for the process according to the invention are, in particular, organic bases, for example amines of the formula (III)

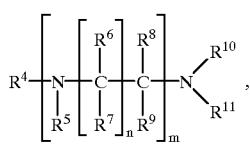

(III)

in which
R⁴ to R¹¹ independently of one another each represent hydrogen or linear or branched $C_1$–$C_4$-alkyl,
m represents 1, 2 or 3 and
n represents 1 or 2.

Such amines are, for example, 1,2-ethylenediamine, diethylenetriamine, triethylenetetramine and tetramethylethylenediamine. Preference is given to 1,2-ethylenediamine. Generally, only one base is used, but if appropriate mixtures of different bases can also be used.

The process according to the invention is carried out in the presence of a protic solvent. Suitable solvents are, eg., alcohols and alcohols in a mixture with other solvents, eg. mixtures with ethers and/or aromatic and/or aliphatic hydrocarbons. If esters serve as starting material (formula (II), R=OR¹), it is expedient to use as solvent the alcohol component present in this ester. Preferably, anhydrous solvents are used, or those which contain less than 5% by weight of water.

For example, 1 to 6 times, preferably 2 to 4 times, the amount by weight of solvent, based on the compound of the formula (II), can be used.

The process according to the invention can be carried out, for example, at temperatures in the range from 0 to 120° C., preferably from 20 to 100° C., particularly preferably from 50 to 80° C.

It is an essential feature of the process according to the invention that the base is added during the reaction. For example, the procedure can be carried out in such a manner that the starting material dissolved in the solvent and the metal are introduced, this mixture is brought to the desired reaction conditions with stirring and then the base is continuously pumped into the reaction vessel in the course of, eg., 5 to 20 hours, preferably 10 to 15 hours. The base can also be introduced in small portions, eg. in portions each of 1 to 10% by weight of the total amount, into the reaction mixture and, after each addition, the mixture can be stirred under reaction conditions for, eg., 3 minutes to 2 hours. Preference is given to continuous addition.

The process according to the invention can be carried out with or without addition of hydrogen. If addition of hydrogen is employed, the pressure can vary within wide ranges. It can be, for example, 1.5 to 200 bar, preferably 5 to 150 bar, in particular 10 to 100 bar.

Theoretically, in the procedure with addition of hydrogen, ½ mol of metal is required for the complete conversion of 1 mol of a compound of the formula (II). It is therefore expedient in this case to use at least 50 mol % of a metal, based on the compound of the formula (II). In the procedure without addition of hydrogen, theoretically, 1 mol of metal is required for the complete conversion of 1 mol of a compound of the formula (II). Therefore, it is expedient in this case to use at least 100 mol % of a metal, based on the compound of the formula (II). It is advantageous to use the respective metal in excess, but amounts greater than 300 mol % of metal (based on the compound of the formula (II)) generally bring no advantages, but are economically disadvantageous. Preferably, 110 to 250 mol %, in particular 120 to 200 mol %, of metal is used, (based on the compound of the formula (II)), independently of whether addition of hydrogen is employed or not.

Theoretically, in the procedure with addition of hydrogen, 1.5 mol of an amine of the formula (III) are required for the complete conversion of 1 mol of a compound of the formula (II). It is therefore expedient in this case to use at least 150 mol % of an amine of the formula (III), based on the compound of the formula (II). Amounts larger than 400 mol % of an amine of the formula (III), based on the compound of the formula (II), do not generally bring advantages in this case, but are economically disadvantageous. Preferably, in this case, 200 to 300 mol %, in particular 220–270 mol %, of an amine of the formula (III) are used, based on the compound of the formula (II). Bases other than amines of the formula (III) can be used in equivalent amounts.

In the procedure without addition of hydrogen, theoretically, 3 mol of an amine of the formula (III) are required for the complete conversion of 1 mol of a compound of the formula (II). It is therefore expedient in this case to use at least 300 mol % of an amine of the formula (III), based on the compound of the formula (II). In this case, amounts larger than 600 mol % of an amine of the formula (III), based on the compound of the formula (II), do not generally bring advantages, but are economically disadvantageous. Preferably, 320 to 500 mol %, in particular 350 to 400 mol % of an amine of the formula (III), based on the compound of the formula (II), are used when the procedure without addition of hydrogen is employed. In this case also, bases other than amines of the formula (III) can be used in equivalent amounts.

If the procedure without addition of hydrogen is employed, the process according to the invention can be carried out, for example, in a stirred tank to be operated at atmospheric pressure. The procedure with addition of hydrogen requires pressure-resistant vessels, eg. autoclaves.

The exhaustively reacted reaction mixture can be worked up, eg., in such a manner that, initially, solid constituents present are separated off, eg. by filtration, then an acid, eg. aqueous hydrochloric acid, is added to the filtrate in order to convert any base still present into the corresponding ammonium salt. The organic phase formed can then be separated off, the aqueous phase can be extracted with a suitable solvent, eg. dichloromethane or toluene, and finally the separated organic phase and the extract can be distilled separately or together. Alternatively, the acid can be added to the filtrate only after the majority of the solvent present therein has been removed.

Another work-up method is initially to dissolve the metal salt present by adding water, then to separate off the metal, to add acid and to proceed further as described above.

In addition to the advantages described above, in the preparation of 2-fluorocyclopropanecarboxylic esters, the frequently particularly desirable cis-isomers can be obtained in particularly good yield and selectivity by the process according to the invention.

Whether the procedure with or without addition of hydrogen is more advantageous depends on the individual case. Without addition of hydrogen, less equipment is used (no pressure-resistant apparatuses, no safety precautions for working with hydrogen), but the efficacy of the process is then not optimal (higher requirement of chemicals, yields and selectivities are not quite so good, more involved work-up and disposal). The procedure without addition of hydrogen is therefore advantageous rather for preparing relatively small amounts of 2-fluoro-1-cyclopropanecarboxylic acid derivatives.

The procedure with addition of hydrogen is advantageous rather for preparing relatively large amounts of 2-fluorocyclopropanecarboxylic acid derivatives, since then higher efficacy can be achieved and the higher capital costs required for this procedure can be recovered more rapidly.

It is surprising that the addition of base according to the invention has advantageous consequences to such a great extent (see the comparison example) and according to the invention the procedure can also be employed without addition of hydrogen.

EXAMPLES

In the examples below, the terms "cis" and "trans" each refer to the position of the fluorine atom with respect to the carboxyl group.

Example 1

270.0 g of ethyl 2-chloro-2-fluorocyclopropanecarboxylate (isomeric ratio cis:trans= 3:2), 1350 ml of ethanol and 135 g of Raney nickel washed free of water with ethanol were introduced into a 3 l stainless steel autoclave equipped with an anchor stirrer. The autoclave was flushed with nitrogen and heated to 60° C. with stirring. 216.0 g of 1,2-ethylenediamine were continuously pumped in at a hydrogen pressure of 50 bar in the course of 15 hours, which corresponded to an addition of 14.4 g/h. The mixture was further stirred for 16 hours. During the entire reaction and the further stirring, a total of 18 l (S.T.P.) of hydrogen were taken up.

The solid constituents of the reaction mixture were then filtered off and washed with 500 ml of ethanol. The filtrate and the washing liquid were combined and then the majority of the ethanol was distilled off. The distillate contained, in addition to ethanol, according to GC analysis, 35.6 g of ethyl trans-2-fluorocyclopropanecarboxylate (42.3%, based on trans starting material used), 4.6 g of ethyl cis-2-fluorocyclopropanecarboxylate (3.6%, based on cis starting material used) and 4.7 g of ethyl butyrate (2.5%, based on the total of cis and trans starting materials used).

250ml of water were added to the distillation residue and a pH of 3 was established using 37% strength by weight hydrochloric acid at a temperature of 22° C. The organic phase which began to separate out in the course of the addition of hydrochloric acid was separated off, the aqueous phase was extracted three times, each time with 100 ml of methylene chloride, the organic phases were combined and dried over sodium sulfate. The combined organic phases no longer contained starting material, according to GC analysis.

The distillation of the combined organic phases at 20 mbar, at a bottom temperature of 35 to 60° C. and an overhead temperature of 38 to 58° C., gave a mixture of 20.1 g of ethyl trans-2-fluorocyclopropanecarboxylate (23.9%, based on trans starting material used), 108.6 g of ethyl cis-2-fluorocyclopropanecarboxylate (85.9%, based on cis starting material used) and 0.5 g of ethyl butyrate (0.3%, based on the total of cis and trans starting materials used).

Example 2

270.0 g of ethyl 2-chloro-2-fluorocyclopropanecarboxylate (isomeric ratio cis:trans= 3:2), 1350 ml of ethanol and 135 g of Raney nickel washed free of water with ethanol were introduced into a 3 l stainless steel autoclave equipped with an anchor stirrer. The autoclave was flushed with nitrogen and heated to 60° C. with stirring. 234.0 g of ethylenediamine were pumped in continuously under a hydrogen pressure of 10 bar in the course of 11 hours. The mixture was further stirred for 14 hours. In total, approximately 18 l (S.T.P.) of hydrogen were taken up.

1400 ml of water were added to the reaction solution at 20° C. The remaining solid constituents were filtered off with suction and the filtrate was adjusted to a pH of 3 using 30% strength by weight hydrochloric acid. The filtrate was extracted six times, each time with 100 ml of toluene. The organic phase was washed with saturated sodium hydrogen carbonate solution. The subsequent distillation gave 48.9 g of ethyl trans-2-fluorocyclopropanecarboxylate (58.2%, based on trans starting material used), 99.9 g of ethyl cis-2-fluorocyclopropanecarboxylate (79.1%, based on cis starting material used) and 6.8 g of ethyl butyrate (3.7%, based on the total of cis and trans starting materials used).

Example 3

30.0 g of ethyl 2-chloro-2-fluorocyclopropanecarboxylate (isomeric ratio cis:trans=3:2), 300 ml of ethanol and 30 g of Raney nickel washed free of water with ethanol were introduced into a 1 l three-neck flask. The flask contents were heated to 80° C. with stirring and 33 g of ethylene diamine were pumped in continuously in the course of 13 hours. The mixture was further stirred for 12 hours. After cooling to room temperature, the solid constituents of the reaction mixture were filtered off with suction. 100 ml of water were added to the filtrate and a pH of 3 was established using 37% strength by weight aqueous hydrochloric acid. The filtrate was extracted five times, each time with 50 ml of toluene, and the combined organic phases were dried using sodium sulfate.

The distillation gave 3.8 g of ethyl trans-2-fluorocyclopropanecarboxylate (40.7%, based on trans starting material used), 9.1 g of ethyl cis-2-fluorocyclopropanecarboxylate (64.8%, based on cis starting material used) and 0.3 g of ethyl butyrate (1.5%, based on the total of trans and cis starting materials used).

Comparison Example

The procedure was followed as in Example 1, but the 1,2-ethylenediamine was not pumped in continuously during the reaction, but the total amount was introduced together with the other reaction components in the autoclave. The methanol distilled off contained, according to GC analysis, 22.9 g of ethyl trans-2-fluorocyclopropanecarboxylate (27.2%, based on trans starting material used), 4.1 g of ethyl cis-2-fluorocyclopropanecarboxylate (3.2%, based on cis starting material used) and 4.5 g of ethyl butyrate (2.4%, based on the total of cis and trans starting materials used). The combined organic phases after the work-up no longer contained starting material and gave, in the distillation, 12.1 g of ethyl trans-2-fluorocyclopropanecarboxylate (14.4%, based on trans starting material used), 86.9 g of ethyl cis-2-fluorocyclopropanecarboxylate (68.8%, based on cis starting material used) and 0.3 g of ethyl butyrate (0.2%, based on the total of cis and trans starting materials used).

It can be seen that the procedure according to the invention involving addition of the amine during the reaction gives considerably better results with regard to selectivity and yield of ethyl cis-2-fluorocyclopropanecarboxylate.

What is claimed is:

1. A process for preparing cyclopropanecarboxylic acid derivatives of the (I)

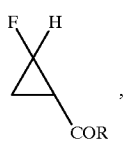

wherein

R represents $OR^1$ or $NR^2R^3$, where $R^1$, $R^2$ and $R^3$ independently of one another each represent a linear or branched $C_1$–$C_4$-alkyl radical, by reacting halogenocyclopropanecarboxylic acid derivatives of the formula (II)

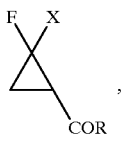

wherein

R has the meaning specified under formula (I) and

X represents chlorine, bromine or iodine with addition of a metal and a base, which comprises adding the base during the reaction and working in a protic solvent, wherein the process is carried out without addition of hydrogen at atmospheric pressure and with addition of 320 to 500 mol % of an amine, based on the compound of the formula (II), of the formula (III), (III)

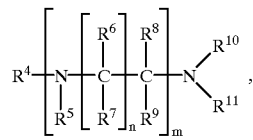

wherein $R^4$ to $R^{11}$ independently of one another represent hydrogen or a linear $C_1$–$C_4$ alkyl group or a branched $C_1$–$C_4$alkyl group.

2. The process as claimed in claim 1, wherein as metal use is made of one or more of the elements of the $2^{nd}$ and/or $8^{th}$ subgroup of the Periodic Table of the Elements.

3. The process as claimed in claim 1, wherein the metal used is Raney nickel.

4. The process as claimed as claim 1, wherein the base used is 1,2-ethylenediamine.

5. The process as claimed in claim 1, wherein the process is carried out at temperatures in the range from 0 to 120° C.

6. The process as claimed in claim 1, wherein from 110 to 250 mol % of metal, based on the compound of the formula (II), are used.

7. The process as claimed in claim 1, wherein the base is continuously pumped into the reaction vessel or is introduced into the reaction vessel in small portions each of 1 to 10% by weight of the total amount and, after each addition, the mixture is stirred under reaction conditions for 3 minutes to 2 hours.

* * * * *